US010533957B2

(12) United States Patent
Momose et al.

(10) Patent No.: US 10,533,957 B2
(45) Date of Patent: Jan. 14, 2020

(54) RADIOGRAPHIC IMAGE GENERATING DEVICE

(71) Applicants: Tohoku University, Sendai-shi (JP); Rigaku Corporation, Akishima-shi (JP)

(72) Inventors: Atsushi Momose, Sendai (JP); Takafumi Koike, Akishima (JP); Masashi Kageyama, Akishima (JP)

(73) Assignees: Tohoku University, Sendai-shi, Miyagi (JP); Rigaku Corporation, Akishima-shi, Tokyo (JP)

( * ) Notice: Subject to any disclaimer, the term of this patent is extended or adjusted under 35 U.S.C. 154(b) by 0 days.

(21) Appl. No.: 16/085,464

(22) PCT Filed: Feb. 20, 2017

(86) PCT No.: PCT/JP2017/006223
§ 371 (c)(1),
(2) Date: Sep. 14, 2018

(87) PCT Pub. No.: WO2017/159229
PCT Pub. Date: Sep. 21, 2017

(65) Prior Publication Data
US 2019/0086341 A1 Mar. 21, 2019

(30) Foreign Application Priority Data
Mar. 17, 2016 (JP) .................. 2016-053760

(51) Int. Cl.
*A61B 6/00* (2006.01)
*G01N 23/041* (2018.01)
(Continued)

(52) U.S. Cl.
CPC ......... *G01N 23/041* (2018.02); *A61B 6/4291* (2013.01); *A61B 6/466* (2013.01);
(Continued)

(58) Field of Classification Search
CPC .............................. A61B 6/484; G01N 23/041
See application file for complete search history.

(56) References Cited

U.S. PATENT DOCUMENTS

| 5,812,629 A | 9/1998 | Clauser |
| 9,006,656 B2 | 4/2015 | Itoh et al. |

(Continued)

FOREIGN PATENT DOCUMENTS

| EP | 3 346 260 A1 | 7/2018 |
| JP | 2012-108098 A | 6/2012 |

(Continued)

OTHER PUBLICATIONS

International Search Report for Application No. PCT/JP2017/006223 dated Apr. 18, 2017.

(Continued)

*Primary Examiner* — Dani Fox
(74) *Attorney, Agent, or Firm* — Seed IP Law Group LLP

(57) ABSTRACT

First ROI pixel values of a first region of interest 101 of a radiographic intensity distribution image 10, and second ROI pixel values of a second region of interest 102 of the radiographic intensity distribution image 10, are acquired. One of the first and second regions of interest is set to be at a position, or vicinity thereof, where a phase difference in the intensity modulation period within the radiographic intensity distribution image, with respect to the other region of interest, becomes π/2. Next, an elliptical locus obtained by plotting the first and second ROI pixel values for each radiographic intensity distribution image is determined. k angle region images are then acquired using the radiographic intensity distribution images corresponding to at least k angle regions that have been obtained by dividing the (Continued)

elliptical locus for each given angle. A radiographic image is then generated using the k angle region images. k is an integer of three or more.

9 Claims, 6 Drawing Sheets

(51) Int. Cl.
  *G06T 7/11* (2017.01)
  *G01N 23/20* (2018.01)
  *G06T 7/00* (2017.01)

(52) U.S. Cl.
  CPC .............. *A61B 6/481* (2013.01); *A61B 6/484* (2013.01); *G01N 23/20075* (2013.01); *G06T 7/0012* (2013.01); *G06T 7/11* (2017.01); *G06T 2207/10116* (2013.01)

(56) References Cited

U.S. PATENT DOCUMENTS

| | | |
|---|---|---|
| 2005/0286680 A1 | 12/2005 | Momose |
| 2013/0181130 A1* | 7/2013 | Itoh ........................ G01N 23/04 250/336.1 |
| 2015/0182178 A1 | 7/2015 | Baturin et al. |
| 2016/0252470 A1 | 9/2016 | Momose |

FOREIGN PATENT DOCUMENTS

| | | |
|---|---|---|
| WO | 2004/058070 A1 | 7/2004 |
| WO | 2015-064723 A1 | 5/2015 |
| WO | 2017-033854 A1 | 3/2017 |

OTHER PUBLICATIONS

S. Bachche et al., "X-ray phase scanning setup for non-destructive testing using Talbot-Lau interferometer," Sep. 16, 2016, Proceedings of SPIE, ISSN 0277-786X, vol. 9964, pp. 99640F-1-9640F-9, 9 pgs.

EPO Communication for corresponding EP Application No. 17766236.8, dated Oct. 15, 2019, 8 pgs.

* cited by examiner

RADIOGRAPHIC IMAGE GENERATING DEVICE

BACKGROUND

Technical Field

The present disclosure relates to technology for observing the structure of a subject, utilizing wave properties of radiation that has passed through the subject, such as X rays.

Description of the Related Art

Radiation of high penetrating power, for example X-rays, is in widespread use as probes for visualizing the inside of a material in fields such as medical image diagnosis, non-destructive testing, security checks, etc. Contrast of an X-ray perspective image depends on difference in X-ray attenuation factor, and a body that strongly absorbs X-rays is rendered as an X-ray shadow.

X-ray absorption power is stronger the more elements are contained that have a larger atomic number. Conversely, for a material that is composed of elements of small atomic number, it can be noted that it is also difficult to obtain contrast, and this is also a principle disadvantage with conventional X-ray perspective images. Accordingly, it has not been possible to obtain sufficient sensitivity with regard to soft biological tissue, organic material, etc.

On the other hand, if the wave properties of X-rays are utilized, it is possible to realize a sensitivity increase of up to about three orders of magnitude compared to general conventional X-ray perspective images. Hereafter this will be referred to as an X-ray phase contrast method. If this technology is applied to observation of materials composed of light elements that do not absorb X-rays well (such as soft biological tissue, organic material, etc.), then since examination becomes possible that was difficult with the conventional methods, such practical application is expected.

A method that uses a transmission grating is known as an approach for realizing a high sensitivity imaging method that utilizes the X-ray phase contrast method (refer to patent publications 1 and 2 below). This is a method for obtaining contrast that shows the structure of a subject by means of a phenomenon whereby an intensity pattern formed by a transmission grating that is being irradiated by X-rays on an X-ray detector varies due to slight refraction and dispersion of X-rays of a subject that is being irradiated with the same X-rays. With this method, it is possible to generally generate absorption images corresponding to conventional perspective images, refractive images showing magnitude of refraction of X-rays by the subject, and scattering images showing magnitude of scattering by the subject. In a case where grating period of a transmission grating that is used is minute, a detector is arranged at a position where the intensity pattern is strongly visible, taking into consideration fractional Talbot effect due to interference effect (so-called diffraction effect) caused by the grating. Also, in a case where the intensity pattern is so fine that it cannot be resolved directly with a detector, one more transmission grating is arranged at that position and it is possible to visualize variations in the intensity pattern by creating a moiré. It should be noted that hereafter the initial transmission grating will be called G1 and the second transmission grating will be called G2. A structure composed of G1 and G2 will be referred to as a Talbot interferometer.

In operating a Talbot interferometer, it is desirable for a spatial interference distance of radiation that is irradiated on G1 to be equal to the G1 period or greater than that. This is because there is a need for radiation waves to be aligned, and with X-rays, for example, this is satisfied by using synchrotron radiation and a microfocus X-ray source. In particular, since a microfocus X-ray source is a radiation source that can be used in a laboratory it is worth noting when considering practical use.

However, output power of a microfocus X-ray source is generally limited, and so an exposure time of from a number of minutes to a few tens of minutes is normally required. An X-ray source that is generally used is higher power than a microfocus X-ray source, but in the first place a spatial coherence required in order to allow operation of an X-ray Talbot interferometer cannot be expected.

Therefore a Talbot-Lau interferometer having a third lattice (hereafter, G0) arranged in the vicinity of a general X-ray source is known. G0 behaves as a multislit. A single slit of G0 will be noted. An X-ray passing through this single slit makes a downstream Talbot interferometer (G1 and G2) function. Specifically, G0 can be construed as virtually constituting a microfocus X-ray source. Attention will focus on X-rays that pass through the next slit in G0. Similarly, the downstream Talbot interferometer is made to operate, but with intensity pattern due to G1 at a G2 position it is possible to adjust period of G0 such that it is offset by exactly one period (strictly speaking, an integral multiple of one period). By doing this, making phase contrast shooting high speed is realized using a conventional bright X-ray source that has low coherence while still generating moiré images using a downstream Talbot interferometer.

Accordingly, it can be recognized that a Talbot-Lau interferometer is a plurality of Talbot interferometers superimposed, and also that G0 is part of a radiation source. It is also possible to arrange only G0 and G1 close to the radiation source, and omit G2, and have a method of shooting the intensity pattern that has been expanded with a direct detector, and this is called a Lau interferometer.

With either configuration, direct use of an intensity pattern or a moiré image that has been stored is scarce, and images that have been stored are processed by a given procedure using a computer, and it is possible to generate and use absorption images, refraction images and scattering images, etc. A fringe scanning method is generally used for this purpose. A fringe scanning method is a method in which either grating is translated in its periodic direction, a plurality of intensity patterns or moiré images are photographed, and image operations are carried out. More specifically, shooting is carried out by translating either grating by 1/M of its period, and image operations are carried out using M images that have been obtained by repeating this process M times. M is an integer of 3 or greater.

In a case where a fringe scanning method using grating translation is adopted, it is assumed that respective gratings that are not translated are stationary between measurements. However, there are cases where from a practical viewpoint there is vibration of the gratings and positional drift of a stage that holds the gratings, which causes vibration and displacement of the moiré fringe, and this in turn may cause serious error in measurement results. At such a time, it is necessary to stabilize the environment in which a Talbot interferometer or Talbot-Lau interferometer is installed, or implement procedures such as to improve rigidity of a stage or frame that holds and moves the grating, or isolate from the source of vibration, etc. However when using the device as a non-destructive testing device in the production field, for example, there may be cases where the surrounding environment is not necessarily favorable. The costs due to assembling a device that is resistant to vibration and drift are also not negligible.

CITATION LIST

Patent Literature

[Patent publication 1] International patent publication WO2004/058070
[Patent publication 2] U.S. Pat. No. 5,812,629

BRIEF SUMMARY

Problems to be Solved

The present disclosure has been conceived in view of the above-described situation. An object of the present disclosure is to provide technology that can make handling of vibration and drift of a grating used in generation of a radiographic image easy.

Means for Solving the Problems

The present disclosure can be expressed as described in at least the following aspects.
(Aspect 1)
A device for generating a radiographic image using a radiographic intensity distribution image, comprising:
an imaging section, a drive section, and a processing section, wherein:
the imaging section is provided with a radiation source, a grating section and an image detection unit;
the radiation source is configured to irradiate radiation towards the grating section;
the image detection unit is configured to acquire a plurality of radiographic intensity distribution images by detecting radiation that has penetrated the grating section at given time intervals;
the grating section is provided with at least one grating that applies a periodic intensity modulation to the radiographic intensity distribution image;
the at least one grating has a periodic structure;
the drive section is configured to move the grating in a direction that crosses an advancement direction of the radiation;
the processing section is provided with a region of interest (ROI) pixel value acquisition section, an elliptical locus determination section, an angle region image acquisition section, and a radiographic image computation section;
the ROI pixel value acquisition section is configured to acquire a first ROI pixel value of a first region of interest within the radiographic intensity distribution image and a second ROI pixel value of a second region of interest within the radiographic intensity distribution image;
one of the first and second regions of interest is set to be at a position, or vicinity thereof, where a phase difference in the intensity modulation period, with respect to the other region of interest, becomes $\pi/2$;
the elliptical locus determination section is configured to determine an elliptical locus that is obtained by plotting the first and second ROI pixel values for each of the radiographic intensity distribution images;
the angle region image acquisition section is configured to obtain k angle region images using the radiographic intensity distribution images corresponding to at least k angle regions that have been obtained by dividing the elliptical locus for each given angle;
the radiographic image computation section is configured to generate the radiographic image using the k angle region images; and
k is an integer of three or more.
(Aspect 2)
The radiographic image generating device of aspect 1, wherein the angle region images are obtained by performing additive averaging of the plurality of radiographic intensity distribution images corresponding to the angle regions.
(Aspect 3)
The radiographic image generating device of aspect 1 or aspect 2, wherein the grating section has at least first and second gratings.
(Aspect 4)
The radiographic image generating device of any one of aspects 1 to 3, wherein the radiation is X-rays.
(Aspect 5)
The radiographic image generating device of any one of aspects 1 to 4, wherein a range of the intensity modulation included in an area of the first and second regions of interest is made $\frac{1}{4}$ or less of one period of the intensity modulation.
(Aspect 6)
The radiographic image generating device of any one of aspects 1 to 5, wherein the elliptical locus determination section is configured to determine the elliptical locus by plotting the first and second ROI pixel values in a rectangular coordinate system for each radiographic intensity distribution image, with the first ROI pixel value as one axis of the rectangular coordinate system and the second ROI pixel value as the other axis of the rectangular coordinate system.
(Aspect 7)
The radiographic image generating device of any one of aspects 1 to 6, wherein the first pixel value is an average value of pixel values included in the first region of interest.
(Aspect 8)
A method for generating a radiographic image using a radiographic intensity distribution image, comprising:
a step of irradiating radiation of a radiation source toward a grating section, the grating section here being provided with at least one grating that applies a periodic intensity modulation to the radiographic intensity distribution image;
a step of acquiring a plurality of the radiographic intensity distribution images by detecting the radiation that has penetrated the grating section at given time intervals;
a step of moving the grating in a direction that intersects advancement direction of the radiation;
a step of acquiring a first region of interest (ROI) pixel value of a first region of interest within the radiographic intensity distribution image and a second ROI pixel value of a second region of interest within the radiographic intensity distribution image, with one of the first and second regions of interest here being set to be at a position, or vicinity thereof, where a phase difference in the intensity modulation period, with respect to the other region of interest, becomes $\pi/2$;
a step of determining an elliptical locus obtained by plotting the first and second ROI pixel values for each radiographic intensity distribution image;
a step of obtaining k angle region images using the radiographic intensity distribution images corresponding to at least k angle regions that have been obtained by dividing the elliptical locus for each given angle, k here being an integer of three or more; and a step of generating the radiographic image using the k angle region images.

(Aspect 9)

A computer program for causing a computer to execute each of the steps described in aspect 8.

This computer program can be stored in an appropriate non-transitory computer-readable storage medium (for example, optical storage medium such as CD-ROM or DVD disk, magnetic storage medium such as hard disk or flexible disk, or magneto optical storage medium such as MO disk). This computer program can be sent via communication lines such as the Internet.

Effect

According to the present disclosure, it becomes possible, in a fringe scanning method that translates a grating and repeatedly performs shooting for each given distance, to make handling of vibration and drift of a grating used in generation of a radiographic image easy.

DETAILED DESCRIPTION

A radiographic image generating device of one embodiment of the present disclosure will be described in the following. This device is for generating a radiographic image (for example, either or all of an absorption image, a refraction image, or a scattering image) using a radiographic intensity distribution image. This device targets either an organism or object other than an organism as a specimen (not illustrated). Also, this device can be used in medical applications or non-medical applications. As an application in non-medical fields, it is possible to exemplify the examination of foodstuffs, industrial parts, or industrial products, but these are not limiting. It is also possible to use this device in a state where a specimen is not used. In this case it is possible to measure distortion of a grating itself.

Figure 1:
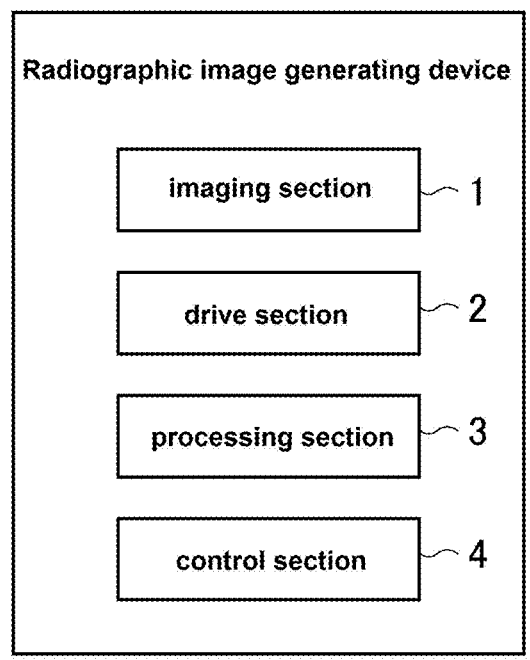
FIG. 1 is a block diagram showing the schematic structure of a radiographic image generating device of one embodiment of the present disclosure.

The radiographic image generating device of this embodiment comprises an imaging section 1, drive section 2, and processing section 3 (refer to FIG. 1). Further, the radiographic image generating device of this embodiment is additionally provided with a control section 4.

(Imaging Section)

Figure 2:
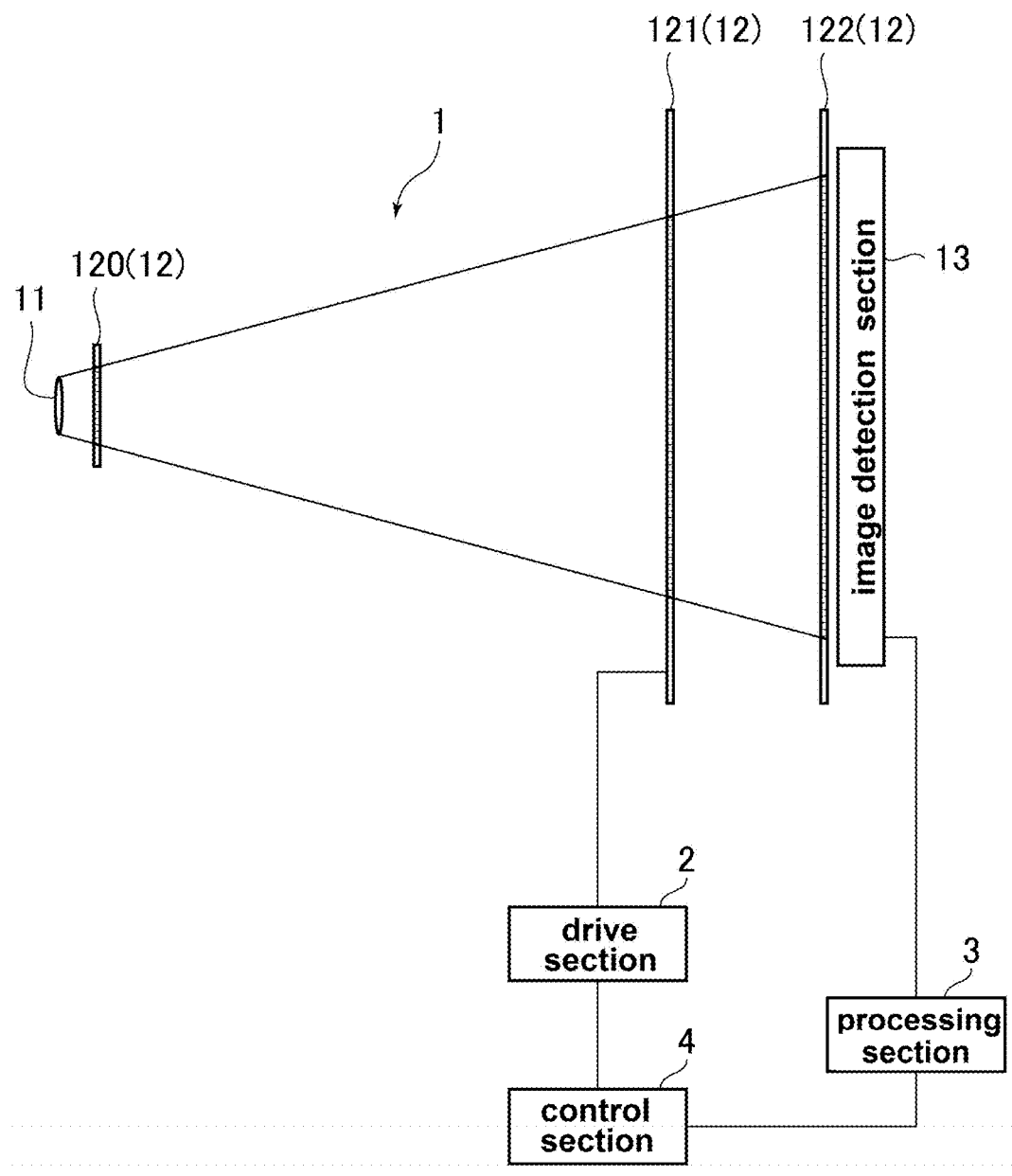
FIG. 2 is an explanatory drawing for showing the structure of the imaging section in FIG. 1.

The imaging section 1 is provided with a radiation source 11, a grating section 12, and an image detection unit 13 (refer to FIG. 2). The radiation source 11 is configured to irradiate radiation towards the grating section 12. Here, as radiation, a type of radiation that has transmissivity with respect to a specimen (not illustrated) is used.

Specifically, with this embodiment, an X-ray source that generates X-rays is used as the radiation source 11. As the radiation source 11 it is possible to use, for example, an X-ray source that causes X-rays (namely, radiation) as a result of irradiation of an electron beam to a target (not illustrated). Specific structure of the radiation source 11 can be made the same as an already known X-ray source, and so more detailed description in this regard is omitted.

The image detection unit 13 is configured to acquire a plurality of radiographic intensity distribution images 10 (refer to FIG. 5 which will be described later) by detecting radiation that has passed through the grating section 12 at given time intervals. Here, the image detection unit 13 of this embodiment can acquire a movie of radiographic intensity distribution images by sequentially acquiring the radiographic intensity distribution image at sufficiently short periods with respect to movement velocity of the grating, which will be described later. In this specification, respective radiographic intensity distribution images constituting a movie will be called a frame image, or simply a frame. It should be noted that an imaging period for the radiographic intensity distribution image does not necessarily need to be fixed, but for convenience of explanation description will be given in the following assuming that there is a fixed imaging period.

The detection section 13 of this embodiment is configured to be able to acquire a radiographic intensity distribution image of radiation that has passed through the grating section 12, that has been arranged on a path from the radiation source section 11 to the detection unit 13. In more detail, the image detection unit 13 has a structure where pixels are arranged in a two-dimensional array horizontally and vertically, and is configured to detect radiation that reaches the pixels through the grating section 12. An image detector that is the same as a conventional image detector may be used as the image detection unit 13, and so more detailed description is omitted.

(Grating Section)

Figure 5:
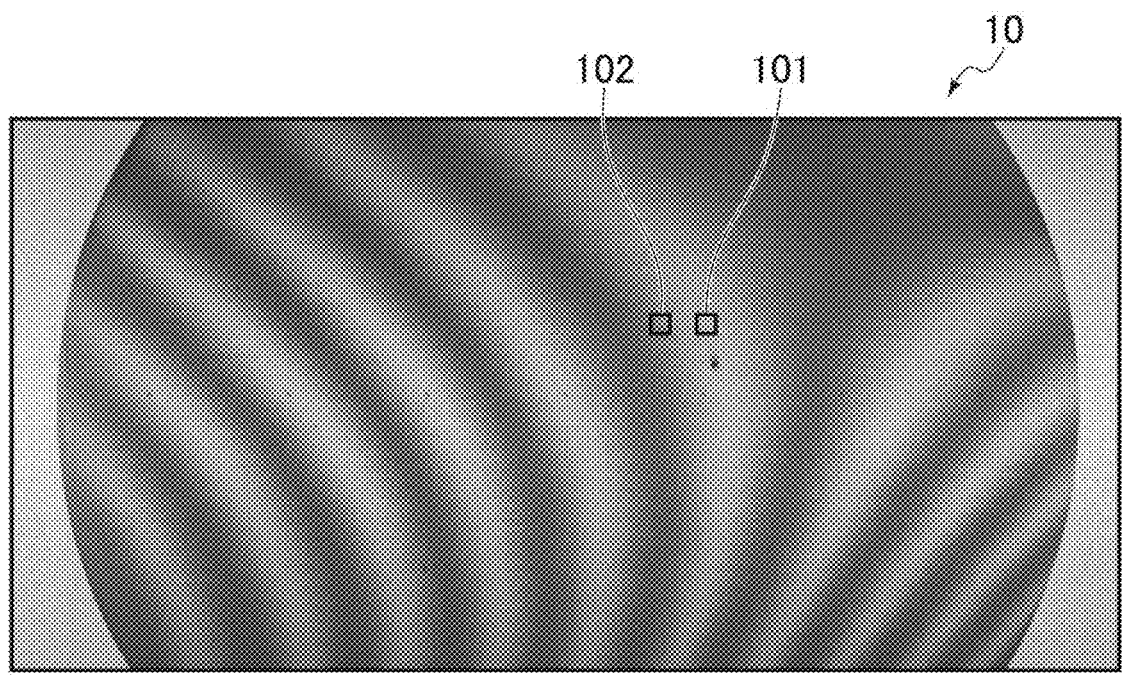
FIG. 5 is an explanatory drawing for describing an overview of a radiographic intensity distribution image used in the image generating method of FIG. 4.

The grating section 12 is provided with at least one grating having a periodic structure that imparts periodic intensity modulation (for example, a moiré fringe or image of the grating itself) for a radiographic intensity distribution image 10 (refer to FIG. 5). The grating section 12 satisfies conditions for mechanical structure and geometric configuration necessary to construct a Talbot interferometer (including the cases of a Talbot-Lau interferometer and a Lau interferometer). However, for this embodiment, conditions for constructing a Talbot interferometer are not required to satisfy conditions in the strict mathematical sense of the word, as long as they are met to an extent that is sufficient to make required examination possible.

More specifically, the grating section 12 of this embodiment is made up of a G0 grating 120, a G1 grating 121 (corresponding to a first grating), and a G2 grating 122 (corresponding to a second grating), all having a periodic structure. A period structure is grating members or slits (not illustrated) that extend in a one dimensional direction and that are arranged periodically, but this is not limiting, and the periodic structure is not particularly limited as long as it has the periodic structure required for operation of the device. A two-dimensional periodic structure is also possible. Also, in this specification, "periodic" is not required to be a strict periodicity as long as there is periodicity to the extent required for device operation.

The G0 grating 120 is a grating for constituting a Talbot-Lau interferometer, which is one type of Talbot interferometer, and uses an absorption type grating. A micro-light source array (i.e., a Talbot interferometer if a single light source is considered) which is a structural element of a Talbot-Lau interferometer is realized by the G0 grating 120. As G1 grating 121, a phase type grating is normally used, but it is also possible to use an absorption type grating. An absorption type grating is used as G2 grating 122. It should be noted that a structure from which arrangement of the G2 grating is omitted is also possible.

(Lau interferometer. Refer to Japanese patent laid open number 2012-16370). Also, in a Lau interferometer, if a radiation source of high spatial coherence is used, such as a micro focus X-ray source or synchrotron radiation, then in the case of shooting with only the G1 grating, with the G0 further omitted, also, shooting of an image of the G1 grating itself (namely an image that has been subjected to intensity modulation) is possible. That is, in this case, operation is possible with only the single grating. It is also possible to have a structure that only uses the G1 grating and G2 grating, with the G0 grating omitted. In this case, however, it is necessary to use radiation having a certain degree of spatial coherences (for example, micro focus X-rays or synchrotron radiation) as the radiation.

In points other than described above, the structures of the G0-G2 gratings 120-122 can be the same as for a conventional Talbot interferometer (including the cases for a Talbot-Lau interferometer and a Lau interferometer), and so more detailed description will be omitted.

(Drive Section)

The drive section 2 is configured to move any of the gratings constituting the grating section 12 in a direction that intersects the advancement direction of radiation. Specifically, the drive section 2 of this embodiment is configured to translate the G1 grating 121 in a direction (the vertical direction in FIG. 2, or direction that is orthogonal to the sheet surface) that substantially intersects the advancement direction of radiation (the right direction in FIG. 2). As the drive section 2, it is possible to use an appropriate mechanism to cause translation of the grating, such as a ball screw, a linear motor, a piezoelectric element, or electrostatic actuator, for example, but this is not limiting. Since it is possible to use an actuator that is used in a conventional fringe scanning method, more detailed description is omitted.

(Processing Section)

Figure 3:
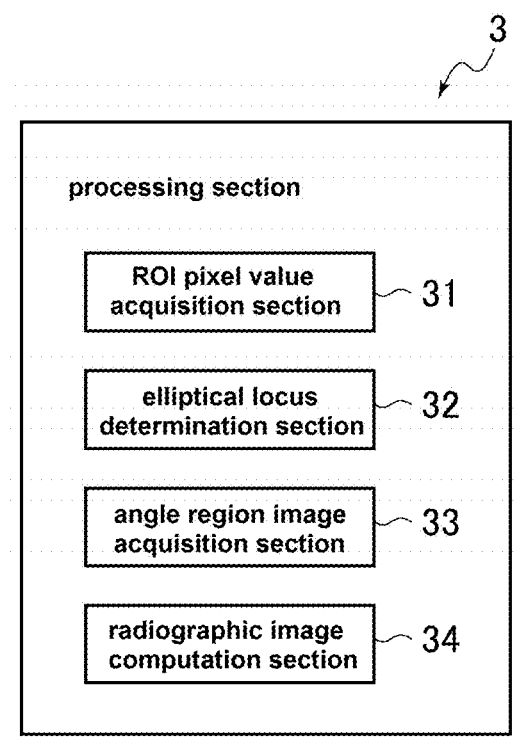
FIG. 3 is a block diagram showing the schematic structure of the processing section in FIG. 1.

The processing section 3 is provided with a region of interest (ROI) pixel value acquisition section 31, elliptical locus determination section 32, angle region image acquisition section 33 and radiographic image computation section 34 (refer to FIG. 3).

The ROI pixel value acquisition section 31 is configured to acquire a first ROI pixel value of a first region of interest 101 (refer to FIG. 5, which will be described later) within the radiographic intensity distribution image and a second ROI pixel value of a second region of interest 102 (refer to FIG. 5, which will be described later) within the radiographic intensity distribution image.

Here, a range of intensity modulation included in the area of the first and second regions of interest 101 and 102 is preferably made ¼ or less of one period of intensity modulation, so that division between the first and second regions of interest 101 and 102 when pixel values have been plotted (refer to FIG. 6, which will be described later) does not become indistinct. If the size of a region of interest is large, an elliptical locus generated in a step that will be described later would become small (that is, plot points will gather at the center). By making the elliptical locus large, it is possible to increase the number of plot points that can be effectively used.

The first pixel value is an average value of pixel values included in the first region of interest 101. An average value here is a value obtained by dividing a total of brightness values for each pixel by a number of pixels. Similarly, the second pixel value is an average value of pixel values included in the second region of interest 102.

One of the first and second regions of interest is set to be at a position, or vicinity thereof, where a phase difference in the intensity modulation period, with respect to the other region of interest, becomes $\pi/2$. This point will be described in detail in the description of an operating method.

The elliptical locus determination section 32 is configured to determine an elliptical locus that is obtained by plotting first and second ROI pixel values for each radiographic intensity distribution image (that is, as a function of frame number).

In more detail, the elliptical locus determination section 32 is configured to determine the elliptical locus by plotting the first and second ROI pixel values in a rectangular coordinate system for each radiographic intensity distribution image, with the first ROI pixel value as one axis of the rectangular coordinate system and the second ROI pixel value as the other axis of the rectangular coordinate system. Detailed structure of the elliptical locus determination section 32 will be described later.

The angle region image acquisition section 33 is configured to obtain k angle region images using the radiographic intensity distribution images corresponding to at least k angle regions that have been obtained by dividing the elliptical locus for each given angle. Here, the angle region images are obtained by performing additive averaging on a plurality of radiographic intensity distribution images corresponding to angle regions (namely radiographic intensity distribution images for frame No. corresponding to an angle region). Also, this k is an integer of three or more, but it is preferable to select an integer that is a large as possible. However, it is necessary to select an integer that is sufficiently smaller than a number of radiographic intensity distribution image frames. Detailed structure of the angle region image acquisition section 33 will also be described later.

The radiographic image computation section 34 is configured to generate a radiographic image using the k angle region images. The radiographic image computation section 34 can use a method that is similar to a generation method for a radiographic image of a conventional fringe scanning method (for example, either or all of an absorption image, a refraction image or a scattering image). If it is assumed that shooting is performed by moving a grating having a grating period of 1/M in a fringe scanning method, the k angle region images correspond to M images of a fringe scanning method.

(Control Section)

The control section 4 is configured to send drive signals to the drive section 2, and so as to be able to move a grating at a given speed. The control section 4 is also configured to be able to return to an initial position if movement amount of the grating reaches an upper limit, and then move the grating again. The control section 4 is also configured to be able to obtain a desired movie (plurality of radiographic intensity distribution images) by synchronizing movement timing of the grating and shooting timing of the image detection unit 13.

(Operation of the Radiographic Image Generation of this Embodiment)

An image generating method that uses the radiographic image generating of this embodiment will be described in the following with further reference to FIG. 4. In the following, a specimen (not shown), as a subject, is arranged at an appropriate position from the radiation source 11 to the image detection unit 13. For example, the specimen can be arranged between the G0 grating 120 and the G1 grating 121. However, the device of this embodiment can be used in order to investigate grating distortion in a state where there is no specimen.

Figure 4:
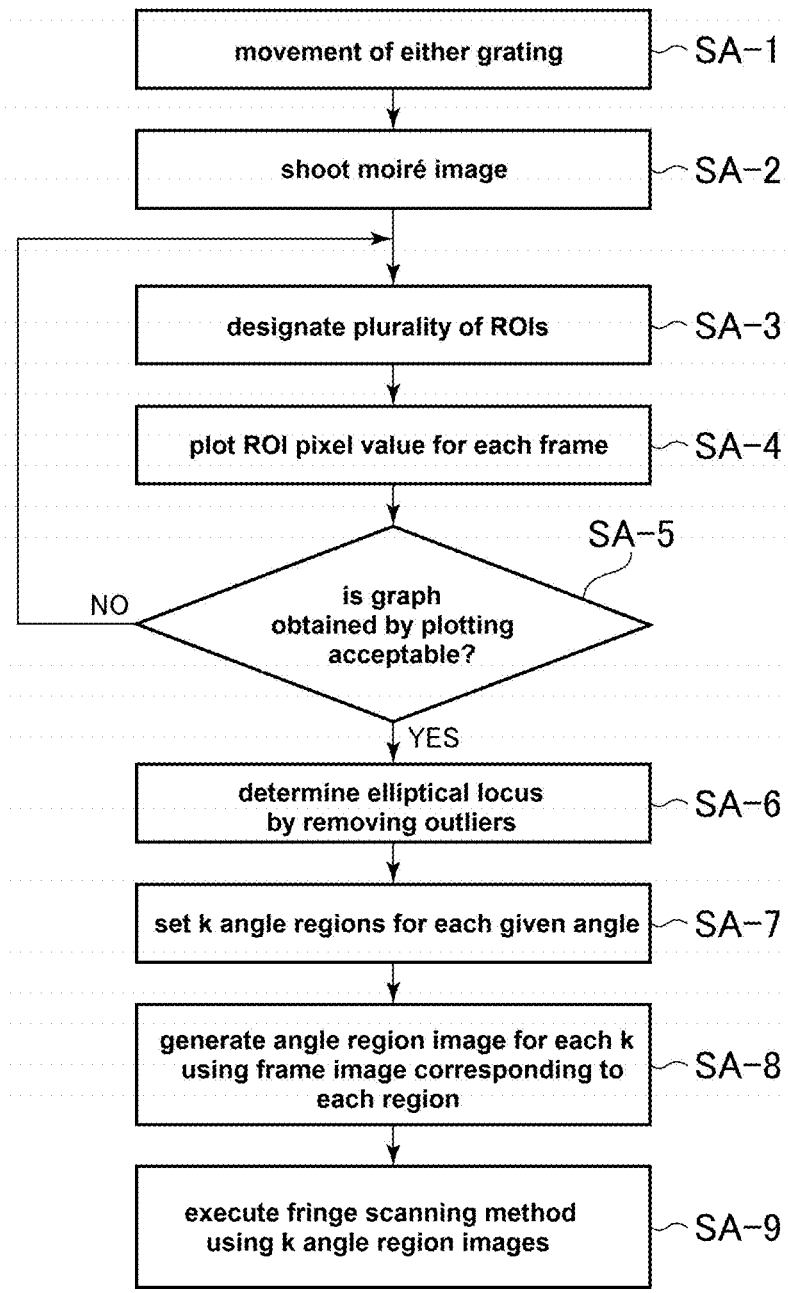
FIG. 4 is a flowchart showing an outline of an image generating method using the device of FIG. 1.

(Step SA-1 of FIG. 4)

First, either the grating of the imaging section 1 (with this example the G1 grating 121) is moved at a given speed for a given time in one direction (direction that is orthogonal to the advancement direction of the radiation) by the drive section 2.

(Step SA-2 of FIG. 4)

Simultaneously with, or before and after, previously described step SA-1, a plurality of radiographic intensity distribution images 10 (refer to FIG. 5) are acquired by the image detection unit 13 of the imaging section 1. In this way it is possible to acquire radiographic intensity distribution images as a movie. The radiographic intensity distribution images 10 that have been acquired are sent to the processing section 3 and saved.

(Step SA-3 of FIG. 4)

Next, first and second regions of interest 101 and 102 are designated on image space of the radiographic intensity distribution images 10 that have been acquired (refer to FIG. 5). This designation can be performed manually, or automatically after the radiographic intensity distribution images 10 have been acquired, based on those images. Here, one of the first and second regions of interest is preferably set to be at a position, or vicinity thereof, where a phase difference in the intensity modulation period, with respect to the other region of interest, becomes $\pi/2$. However, this phase difference does not need to be strict. Also, as will be described later, in a case where there is an inadequate phase difference a procedure is executed recursively, and it is possible to set an arbitrary phase difference in initial settings. In this way, in cases where there is an appropriate phase difference as a result of recursively repeating processing also, it is possible to interpret that setting processing for the appropriate phase difference has been performed. Also, although region of interest designation processing can be performed automatically by the system, it can also be performed by the user.

The first and second regions of interest 101 and 102 are preferably selected as a bright section and intermediate section, or a dark section and an intermediate section, of the intensity modulation period of the radiographic intensity distribution images 10. When a phase difference between the two regions is exactly $\pi/2$, a cycle of fluctuation of the two becomes a sine and cosine relationship, and an obtained elliptical locus becomes circular.

If the first and second regions of interest have been stipulated on the image space, pixel values within these regions change for every frame (periodically change), as a result of change of image for each frame (that is, a movie). It should be noted that here it is assumed that the radiographic intensity distribution images 10 include periodic intensity modulation.

Areas of the first and second regions of interest 101 and 102 are preferably sufficiently small. For example, a range of intensity modulation included in areas of the first and second regions of interest 101 and 102 is preferably made ¼ or less of one period of the intensity modulation, and more preferably ⅙ or less.

Also, positions of the first and second regions of interest 101 and 102 are preferably at positions where the radiation intensity in the image space is strong. Generally, radiation intensity becomes low close to the periphery of the image space. If regions of interest are set at this type of location, there is a problem in that a SN ratio of the ROI pixel values deteriorates. By setting regions of interest at positions where radiation intensity is strong, the SN ratio is improved, and it is possible to improve precision of a radiographic image that is obtained.

(Step SA-4 of FIG. 4)

Next, the ROI pixel value acquisition section 31 acquires pixel values that exist within the first and second regions of interest 101 and 102 as first pixel values and second pixel values. The first pixel value is an average value of pixel values included in the first region of interest 101. Similarly, the second pixel value is an average value of pixel values included in the second region of interest 102. However, it is also possible to use total value instead of average value by making each region of equal size.

Figure 6:
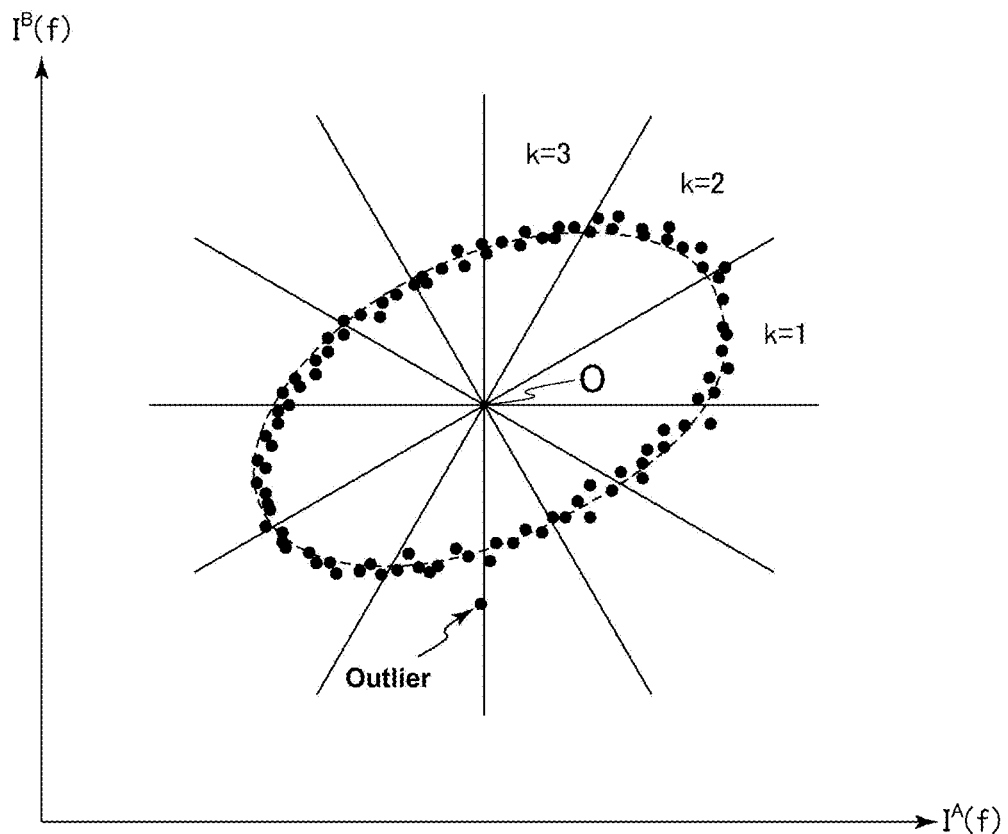
FIG. 6 is a graph on which ROI pixel values are plotted, with the horizontal axis being first ROI pixel values and the vertical axis being second ROI pixel values.

Next, the elliptical locus determination section 32 plots the first and second pixel values that have been obtained as functions of a frame (refer to FIG. 6). For example, the first pixel values are made IA(f), and the second pixel values are made IB(f). Here, f is frame No. If this is done it is possible to obtain a set of pixel values I(f)=(IA(f),IB(f)) for each frame. This I(f) is plotted on a rectangular coordinate system, for example, for each frame (that is, as a function of frame No.). Using points that have been plotted it is possible to determine an elliptical locus. As a method for determining the elliptical locus, it is possible to use an ellipse approximation technique that uses a least squares method, but this is not limiting.

(Step SA-5 of FIG. 4)

Next, the elliptical locus determination section 32 determines whether or not a graph that has been obtained from the plots is appropriate. As a determination reference, there is length of the short axis being sufficiently long as to make it possible to divide data on the ellipse (that is, the graph is close to circular). A specific determination reference can be obtained experimentally, for example. For example, it is possible to use the length of the short axis being ½ or more of the length of the long axis as a reference.

If the result of determination is that the graph is not appropriate (for example, length of the short axis is too short), processing returns to step SA-3, regions of interest are designated again, and the above-described operations are recursively performed. It should be noted that as a shape of the ellipse that is obtained from the plots, a shape that is close to a true circle is preferable, but a true circle is not necessary and the graph may have an elliptical shape to the extent that data can be appropriately divided. Also, in this specification the term ellipse includes a true circle.

(Step SA-6 of FIG. 4)

Next, the elliptical locus determination section 32 removes outliers. As a method of removing outliers, it is possible to use various methods. This can be done as described in the following, for example. First, an initial shape of an ellipse is determined by a least squares method from the graph that was obtained in step SA-4, without setting outliers. In this way, center of the ellipse is provisionally determined. 360° around this center are equally divided into k regions. For frames included in respective divided regions, distances from a temporary center to pixel value group I(f) are calculated, and an average value of these distances is obtained. For frames in which distance of respective groups of pixel values are not within a range of ±5% of average value of distance, those pixel values are removed. In this way, outliers are removed for the whole of the ellipse, an ellipse shape is obtained again by a least squares method using points that remain, the ellipse center is updated, and the sorting described above is performed for distances from the center to the group of pixel values. After that, this is repeated until there are no points to be removed, and a final elliptical locus is determined.
(Step SA-7 of FIG. 4)

Next, the angle region image acquisition section 33 divides the elliptical locus into k angle regions for each given angle, with a center O of the final elliptical locus (refer to FIG. 6) as a reference. Here, the given angle is made 360°/k. k is an integer of 3 or greater. In the illustrated example, k=12. In order to improve precision of the radiographic image that is obtained, a number of partitions k is preferably increased. In that case, in accordance with the number of k, a number of frames obtained in a single period of the intensity modulation is also preferably increased. Also at least three or more points (a single point corresponds to a single frame) are preferably contained in a single angle region. It should be noted that k in this step does not need to be the same as k in the previous step, but it is actually preferable if they are the same.
(Step SA-8 of FIG. 4)

Next, the angle region image acquisition section 33 averages frame images corresponding to points contained in each region, and generates k angle region images. For example, if it is set that 10 frames exist (namely 10 points exist) in a given (namely an ith) angle region, then averaging is performed for each pixel of those 10 frames, and it is possible to generate a single angle region image.
(Step SA-9 of FIG. 4)

Next, the radiographic image computation section 34 performs the same computation as with conventional fringe scanning using the k angle region images that have been obtained, and can generate a desired radiographic image. Since the radiographic image generating method itself is the same as a conventional method detailed description regarding this method is omitted.

With a conventional fringe scanning method, it is assumed that movement distance of a grating that is translated is known to be accurate. When a relative positional relationship of the gratings during execution of a fringe scanning operation is not constant due to distortion of the entire device caused by temperature drift, for example, there is a risk of serious errors arising in the fringe scanning method computational results. Also, when the device is oscillating, namely when relative position of the grating is oscillating, in a case where oscillation period is shorter than shooting time of each step using a fringe scanning method, the effect of that oscillation appears as lowering of sharpness of a moiré fringe that is generated. In particular, when this effect is not constant in each step of the fringe scanning method, there is a risk of serious errors arising in the fringe scanning method computational results. This embodiment can be said to be a self-solving type fringe scanning method whereby data is acquired with steps of the fringe scanning made minute, the effect of this type of drift and oscillation is detected from acquired data, and desired fringe scanning method computation is implemented. The effects of drift and comparatively gentle oscillation can be detected as an effect of a moiré fringe moving. Even if a phase difference to be photographed in an ith frame per se is photographed in an i+1th frame due to oscillation and distortion of the grating, it is only necessary to perform processing of that phase difference as an image that belongs to the i+1th angle region. The effect of comparatively fast oscillation appears as a lowering of sharpness of a moiré fringe. Specifically, in an argument of the elliptical locus, a group of pixel values result in appearing at a position that is close to the center of the ellipse, and this group of pixel values is excluded.

Although not mentioned up to now, in a case where intensity of the X-ray source fluctuates unexpectedly for any reason also, it is easy for a group of pixel values to fall away from the elliptical locus, and this effect can also be avoided with this embodiment.

As has been described above, using this embodiment, it is possible to realize a robust fringe scanning method, even in cases where there is drift and oscillation in relative position of a grating, and further when there is instability of an X-ray source. In this way there is the advantage that it is possible to devise simplification of device structure and alleviation of installation conditions. Also, according to this embodiment, there is no risk of deterioration in precision of a radiographic image that is obtained, even if there is slight distortion of a manufactured grating itself. Accordingly, with the device of this embodiment it is possible to suppress device costs and operating costs.

It should be noted that the descriptions of the above-described embodiments and practical example are merely examples, and do not show the essential structure of the present disclosure. The structure of each part is not limited to the above description as long as it falls within the scope of the disclosure.

For example, with the previously described embodiment, an X-ray source has been used as the radiation source section, but it is also possible to use another radiation source that has transmissivity with respect to the specimen, for example, a neutron source. Obviously, in this case, the detection section is capable of detecting the radiation source that is used.

Also, with the previously described embodiment the number of regions of interest was made two, and ROI pixel values were plotted two-dimensionally, but the number of regions of interest may be made three and the ROI pixel values plotted three-dimensionally, and it is also possible to construct an ellipsoid (three-dimensional shape) and raise precision. An ellipsoid is also included in the concept of an ellipse in this specification. In this case, a given angle is determined with a solid angle. Obviously the number of regions of interest can also be four or more, and pixel values plotted in a space of the corresponding number of dimensions. A shape that is generated by plotting in a multi-dimensional space in this way is also included in the concept of an ellipse in this specification. It is possible to set a way in which the given angle is acquired in accordance with the number of dimensions used.

Also, the device of this embodiment may also be used in shape measurement of a grating itself, by acquiring the structure of the grating itself in a state where there is no specimen. Generally, since the grating has an extremely fine structure, there is distortion to the grating itself to a certain extent. This type of distortion is not specially intended and occurs naturally with normal manufacturing methods. It is obviously possible to manufacture a grating so as to intentionally impart distortion.

DESCRIPTION OF THE NUMERALS 1 imaging section
11 radiation source 12 grating section
120 G0 grating
121 G1 grating
122 G2 grating
13 image detection unit
2 drive section
3 processing section
31 ROI pixel value acquisition section
32 elliptical locus determination section
33 angle region image acquisition section
34 radiographic image computation section
4 control section
10 radiographic intensity distribution image
101 first region of interest
102 second region of interest
IA first ROI pixel value
IB second ROI pixel value
k number of elliptical locus divisions The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A device for generating a radiographic image using a radiographic intensity distribution image, comprising:
    an imaging section,
    a drive section, and
    a processing section, wherein:
        the imaging section comprises a radiation source, a grating section, and an image detection unit;
        the radiation source is configured to irradiate radiation towards the grating section;
        the image detection unit is configured to acquire a plurality of radiographic intensity distribution images by detecting radiation that has penetrated the grating section at given time intervals;
        the grating section has at least one grating that applies a periodic intensity modulation to the radiographic intensity distribution image;
        the at least one grating has a periodic structure;
        the drive section is configured to move the at least one grating in a direction that crosses an advancement direction of the radiation;
        the processing section comprises a region of interest (ROI) pixel value acquisition section, an elliptical locus determination section, an angle region image acquisition section, and a radiographic image computation section;
        the ROI pixel value acquisition section is configured to acquire a first ROI pixel value of a first region of interest within the radiographic intensity distribution image and a second ROI pixel value of a second region of interest within the radiographic intensity distribution image;
        one of the first and second regions of interest is set to be at a position, or vicinity thereof, where a phase difference in the intensity modulation period, with respect to the other region of interest, becomes $\pi/2$;
        the elliptical locus determination section is configured to determine an elliptical locus that is obtained by plotting the first and second ROI pixel values for each of the radiographic intensity distribution images;
        the angle region image acquisition section is configured to obtain k angle region images using the radiographic intensity distribution images corresponding to at least k angle regions that have been obtained by dividing the elliptical locus for each given angle;
        the radiographic image computation section is configured to generate the radiographic image using the k angle region images; and
        k is an integer of three or more.

2. The radiographic image generating device of claim 1, wherein the angle region images are obtained by performing additive averaging of the plurality of radiogaphic intensity distribution images corresponding to the angle regions.

3. The radiographic image generating device of claim 1, wherein the grating section has at least first and second gratings.

4. The radiographic image generating device of claim 1, wherein the radiation is X-rays.

5. The radiographic image generating device of claim 1, wherein a range of the intensity modulation included in an area of the first and second regions of interest is made ¼ or less of one period of the intensity modulation.

6. The radiographic image generating device of claim 1, wherein the elliptical locus determination section is configured to determine the elliptical locus by plotting the first and second ROI pixel values in a rectangular coordinate system for each radiographic intensity distribution image, with the first ROI pixel value as one axis of the rectangular coordinate system and the second ROI pixel value as the other axis of the rectangular coordinate system.

7. The radiographic image generating device of claim 1, wherein the first pixel value is an average value of pixel values included in the first region of interest.

8. A method for generating a radiographic image using a radiographic intensity distribution image, comprising:
    a step of irradiating radiation of a radiation source toward a grating section, wherein the grating section comprises at least one grating that applies a periodic intensity modulation to the radiographic intensity distribution image;
    a step of acquiring a plurality of the radiographic intensity distribution images by detecting radiation that has penetrated the grating section at given time intervals;
    a step of moving the at least one grating in a direction that intersects advancement direction of the radiation;
    a step of acquiring a first region of interest (ROI) pixel value of a first region of interest within the radiographic intensity distribution image and a second ROI pixel value of a second region of interest within the radiographic intensity distribution image, wherein one of the first and second regions of interest is set to be at a position, or vicinity thereof, where a phase difference in the intensity modulation period, with respect to the other region of interest, becomes $\pi/2$;

a step of determining an elliptical locus obtained by plotting the first and second ROI pixel values for each radiographic intensity distribution image;

a step of obtaining k angle region images using the radiographic intensity distribution images corresponding to at least k angle regions that have been obtained by dividing the elliptical locus for each given angle, wherein k is an integer of three or more; and a step of generating the radiographic image using the k angle region images.

9. A non-transitory computer-readable medium having computer program instructions stored thereon, wherein execution of the computer program instructions by a computer causes the computer to:

irradiate radiation of a radiation source toward a grating section, wherein the grating section comprises at least one grating that applies a periodic intensity modulation to the radiographic intensity distribution image;

acquire a plurality of the radiographic intensity distribution images by detecting radiation that has penetrated the grating section at given time intervals;

move the at least one grating in a direction that intersects advancement direction of the radiation;

acquire a first region of interest (ROI) pixel value of a first region of interest within the radiographic intensity distribution image and a second ROI pixel value of a second region of interest within the radiographic intensity distribution image, wherein one of the first and second regions of interest is set to be at a position, or vicinity thereof, where a phase difference in the intensity modulation period, with respect to the other region of interest, becomes $\pi/2$;

determine an elliptical locus obtained by plotting the first and second ROI pixel values for each radiographic intensity distribution image;

obtain k angle region images using the radiographic intensity distribution images corresponding to at least k angle regions that have been obtained by dividing the elliptical locus for each given angle, wherein k is an integer of three or more; and generate the radiographic image using the k angle region images.

* * * * *